United States Patent
Ben Chaabane et al.

(10) Patent No.: US 8,956,846 B2
(45) Date of Patent: Feb. 17, 2015

(54) CELLULASE PRODUCTION METHOD BASED ON THE REGULATION OF THE DISSOLVED OXYGEN PRESSURE OSCILLATION IN THE CULTURE MEDIUM

(75) Inventors: Fadhel Ben Chaabane, Paris (FR); Celine Cohen, Paris (FR)

(73) Assignee: IFP Energies nouvelles, Rueil-Malmaison Cedex (FR)

(*) Notice: Subject to any disclaimer, the term of this patent is extended or adjusted under 35 U.S.C. 154(b) by 466 days.

(21) Appl. No.: 13/070,804

(22) Filed: Mar. 24, 2011

(65) Prior Publication Data
US 2011/0236954 A1 Sep. 29, 2011

(30) Foreign Application Priority Data

Mar. 26, 2010 (FR) ...................................... 10 01211

(51) Int. Cl.
- *C12N 9/42* (2006.01)
- *C12N 9/24* (2006.01)
- *C12N 1/14* (2006.01)
- *C12P 21/00* (2006.01)

(52) U.S. Cl.
CPC ................. *C12N 9/2434* (2013.01); *C12N 1/14* (2013.01); *C12N 9/2437* (2013.01); *C12N 9/2477* (2013.01); *C12P 21/00* (2013.01)
USPC ........ 435/209; 435/200; 435/243; 435/254.6; 435/256.7; 435/71.1

(58) Field of Classification Search
None
See application file for complete search history.

(56) References Cited

U.S. PATENT DOCUMENTS

| 4,952,505 A | 8/1990 | Cho |
| 2006/0177917 A1 | 8/2006 | Warzywoda et al. |
| 2008/0032371 A1* | 2/2008 | Dicosimo et al. ............. 435/147 |

FOREIGN PATENT DOCUMENTS

EP 1690944 A1 8/2006

OTHER PUBLICATIONS

T. Yano et al. "Fed-batch culture of methanol-utilizing bacterium with DO-stat" J. Ferment. Bioeng. 56:416-420. (1978).*
H.K. Lim et al. "Dissolved-oxygen-stat controlling two variables for methanol induction of rGuamerin in *Pichia pastoris* and its application to repeated fed-batch", Applied Micribiol. Biotechnol. 62:342-348. (2003).*
M.J. Bailey et al. Efficient cellulase production by *Trichoderma reesei* in continuous cultivation on lactose medium with a computer-controlled feeding strategy,Applied Micribiol. Biotechnol. 62:156-162. (2003).*
Reczey, K. et al.: "Cellulase Production by *T. reesei*," Biosource Technology, vol. 57, No. 1, 1996, pp. 25-30, XP-002598219.
Search Report, dated Sep. 6, 2010, issued in corresponding application FR 10/01211.

* cited by examiner

*Primary Examiner* — Rebecca Prouty
(74) *Attorney, Agent, or Firm* — Millen, White, Zelano & Branigan, P.C.

(57) ABSTRACT

The present invention relates to a method of producing cellulolytic and/or hemicellulolytic enzymes by a cellulolytic microorganism in a stirred and aerated bioreactor, comprising a growth stage in the presence of a carbon source and a production stage in the presence of a carbon-containing inductive substrate, wherein the supply of carbon-containing inductive substrate during the production stage is regulated by an oscillation of the dissolved oxygen partial pressure in the medium.

13 Claims, 1 Drawing Sheet

CELLULASE PRODUCTION METHOD BASED ON THE REGULATION OF THE DISSOLVED OXYGEN PRESSURE OSCILLATION IN THE CULTURE MEDIUM

FIELD OF THE INVENTION

The invention relates to a method of producing enzymes for lignocellulosic biomass hydrolysis.

BACKGROUND OF THE INVENTION

Lignocellulosic biomass is characterized by a complex structure consisting of three main polymers: cellulose, hemicellulose and lignin. The cellulose and possibly the hemicelluloses are the targets of enzymatic hydrolysis, but they are not directly accessible to enzymes.

These substrates therefore have to undergo a pretreatment prior to the enzymatic hydrolysis stage. The pretreatment aims to modify the physical and physico-chemical properties of the lignocellulosic material in order to improve the accessibility of the cellulose trapped in the lignin and hemicellulose matrix. These pretreatments can be of different types: acidic boiling, alkaline boiling, steam explosion or Organosolv processes can be mentioned.

The enzymatic hydrolysis stage allows cellulose and hemicelluloses to be converted to sugars using cellulolytic and/or hemicellulolytic enzymes. Microorganisms such as fungi belonging to the *Trichoderma, Aspergillus, Penicillium* or *Schizophyllum* genera, or anaerobic bacteria belonging for example to the *Clostridium* genus, produce these enzymes containing notably cellulases and hemicellulases, suited for total hydrolysis of the cellulose and of the hemicelluloses.

The sugars obtained by lignocellulosic biomass hydrolysis are pentoses (mainly xylose and arabinose), disaccharides (cellobiose) and glucose that can be fermented by microorganisms. Glucose can for example be readily converted to ethanol by the *Saccharomyces cerevisiae* yeast during the alcoholic fermentation stage.

Finally, a distillation stage allows to separate and to recover the fermentation product thus obtained, ethanol in the previous case, from the fermentation must.

Various technico-economic studies show the necessity of reducing the cost linked with the enzymatic hydrolysis stage in order to bring the cost of the ethanol produced to values close to the ethanol obtained from starch.

One means of decreasing the costs consists in optimizing the operating conditions of the cellulase production method so as to increase productivity or to obtain an enzymatic cocktail having an improved specific activity.

The most commonly used microorganism for cellulase production is the filamentous *Trichoderma reesei* fungus. The wild strains have the ability to secrete, in the presence of an inductive substrate such as cellulose or lactose for example, an enzymatic complex suited for cellulose hydrolysis. The enzymes of the enzymatic complex comprise three major types of activities: endoglucanases, exoglucanases and cellobiases.

The complex cellulase synthesis regulation mechanisms require particular implementations for their production in a reactor. Using strains that are not sensitive to catabolic repression and soluble inductive substrates usable on a large scale, such as lactose, has allowed to obtain significant productions of the order of 40 g/L extracellular proteins by *T. reesei* CL 847 according to a method described in Bioresource Technol. (1992) 39, 125-130. In this method, fermentation takes place in two stages, a first stage of batch production of *T. reesei* cells and a second stage of fed batch supply of the inducer at a rate preventing accumulation thereof in the medium.

The physiological state of the microorganism being not always maintained at its optimum level for enzyme production, phenomena of growth of nonproductive cells, or of unwanted cell lysis or sporulation leading to an enzyme productivity decrease, are observed in some cases. The balance between optimum production states and unwanted physiological states is rather sensitive. Bailey et al. (Appl. Microbiol. Biotechnol. 2003 62: 156-162) have shown that the productivity of cellulases is optimum when the cells are in a state close to the carbon-containing substrate limitation in the medium. A method of adding carbon-containing substrate using monitoring the basic consumption rate used for pH control has been proposed.

Furthermore, the method described in patent EP-B1-0,448, 430 requires an optimized sugar supply rate of 35 to 45 mg·g$^{-1}$·h$^{-1}$. In fact, too high a supply rate causes an accumulation of carbon-containing substrate in the medium, which leads to a metabolic change towards biomass production instead of enzyme production. On the other hand, too low a supply rate leads to biomass lysis and to production loss. Furthermore, *Trichoderma reesei* excretes then more proteases reconsuming part of the cellulases produced.

The present invention provides a method allowing to maintain the microorganism in the state corresponding to its optimum level for enzyme production.

SUMMARY OF THE INVENTION

The invention provides a method of producing cellulolytic and/or hemicellulolytic enzymes wherein the supply of carbon-containing inductive substrate required for the production stage is regulated by an oscillation of the dissolved oxygen pressure in the medium.

DETAILED DESCRIPTION

Figure 1:
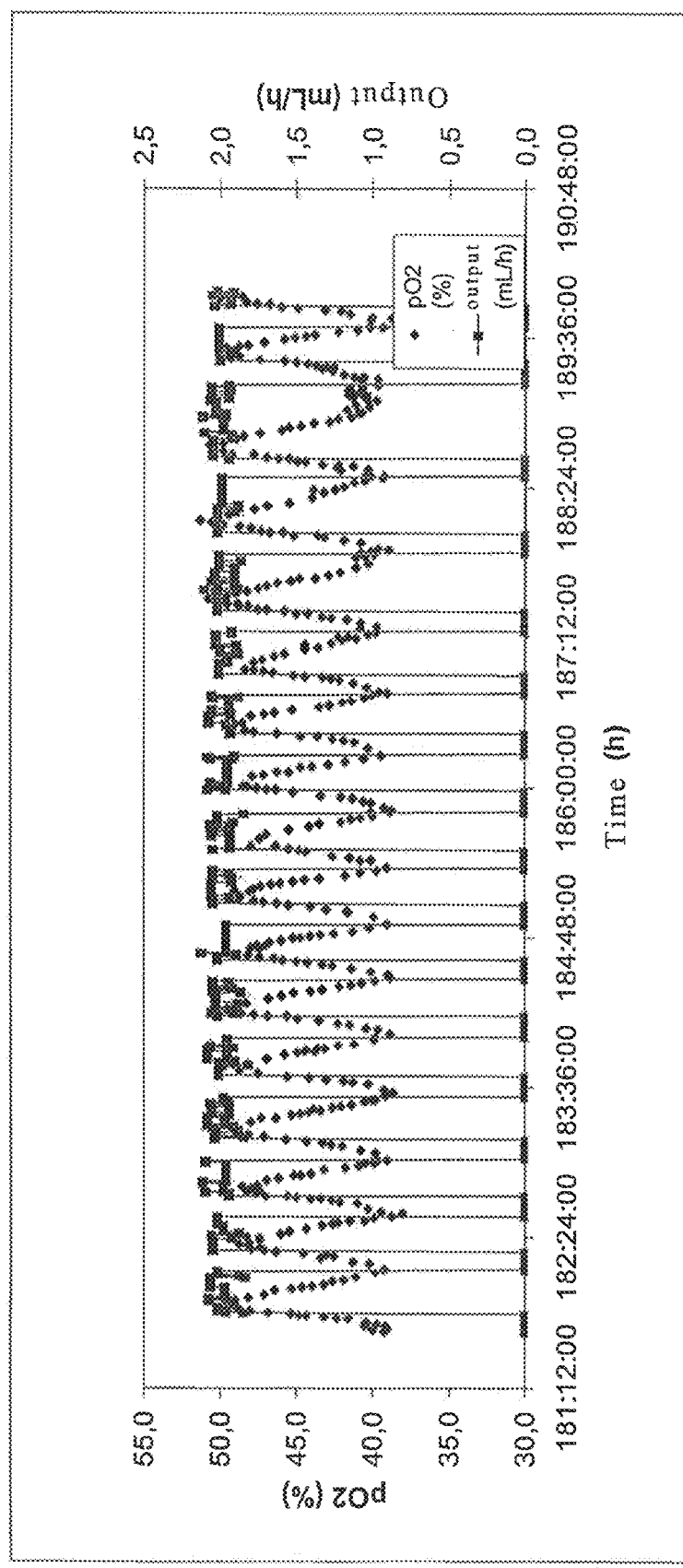
FIG. 1 shows the record of the dissolved oxygen pressure in the medium as a function of time, as well as the rate of supply of the carbon-containing substrate.

The present invention relates to a method of producing cellulolytic and/or hemicellulolytic enzymes by a cellulolytic microorganism in a stirred and aerated bioreactor, comprising a growth stage in the presence of a carbon source and a production stage in the presence of a carbon-containing inductive substrate, wherein the supply of carbon-containing inductive substrate during the production stage is regulated according to the dissolved oxygen partial pressure in the growth medium, said pressure oscillating between two values $Po_{2min}$ and $Po_{2max}$, the value of $Po_{2min}$ being greater than the critical pressure $Po_{2critical}$ below which the activity of the microorganism is affected and less than 95% of the saturation oxygen partial pressure $Po_{2sat}$ set when starting the bioreactor, and the value of $Po_{2max}$ being at least 5% greater than $Po_{2min}$, addition of the carbon-containing inductive substrate being started as soon as the dissolved oxygen partial pressure in the medium is greater than value $Po_{2max}$ and stopped as soon as the dissolved oxygen pressure in the medium is below value $Po_{2min}$.

This method allows to optimize the production of cellulolytic and/or hemicellulolytic enzymes while maintaining the cells in an optimum productivity phase.

By means of the method according to the invention, it is possible to produce an enzymatic cocktail exhibiting a specific activity up to 50% higher than that of enzymes obtained with a conventional production method where the carbon limitation is imposed with a constant supply rate.

Furthermore, this method affords the advantage of being robust and simple to implement. It also allows to avoid the accumulation of sugars in the medium, which leads to biomass formation at the expense of enzyme production.

The microorganism strains used are cultivated in stirred and aerated bioreactors under conditions compatible with their growth and enzyme production.

At fermentation start, the bioreactor is saturated with oxygen and the dissolved oxygen partial pressure corresponding to saturation is denoted by $Po_{2sat}$.

The carbon source used for the growth stage is fed into the bioreactor so as to have an initial sugar concentration for the start of the production stage ranging between 15 and 60 g/L.

During the growth stage, aeration is set at a value selected by the operator and the oxygen partial pressure $Po_2$ is regulated at a percentage, defined by the operator, of the saturation pressure through stirring. The oxygen partial pressure in the medium has to be greater than the critical oxygen pressure $Po_{2critical}$ below which the activity of the microorganism is affected.

This value of $Po_{2critical}$ is known to the person skilled in the art and it depends on the microorganism used. It can be defined as the pressure below which the microorganism metabolism is affected by a decrease in the cell viability or in the production of metabolites of interest.

During the production stage, stirring and aeration in the bioreactor are set at a predetermined value allowing to have an oxygenation capacity for said bioreactor corresponding to a Kla value ranging between 50 and 150 $h^{-1}$ depending on the biomass initially considered.

In the method according to the invention, the carbon-containing inductive substrate is introduced after depletion of the initial substrate: it is the start of the production stage. The oxygen consumption rate is proportional to the rate of consumption of carbon-containing inductive substrate by the microorganism.

Thus, a small accumulation of sugar in the fermenter leads to a fall in the oxygen partial pressure. When the measured oxygen partial pressure reaches a minimum value $Po_{2min}$, the system regulation stops the addition of carbon-containing inductive substrate. This stop causes a decrease in the rate of consumption of carbon-containing inductive substrate at a time when the concentration thereof is close to the affinity constant Ks of the microorganism for the carbon-containing substrate. This stop also causes a decrease in the oxygen consumption rate, which leads to an oxygen partial pressure increase up to a value $Po_{2max}$. When pressure $Po_{2max}$ is reached, the system regulation starts again the carbon-containing inductive substrate supply pump.

Values $Po_{2min}$ and $Po_{2max}$ between which the dissolved oxygen partial pressure in the fermentation medium oscillates are determined by the operator from the oxygen saturation pressure $Po_{2sat}$, depending on the microorganism strains used and/or on the fermentation medium.

The amplitude of the oscillations between values $Po_{2min}$ and $PO_{2max}$ regulates the time interval between the times when the carbon-containing inductive substrate is injected and the times when injection is stopped.

Thus, the cells are consequently maintained in a state close to the carbon limitation (at a concentration close to Ks), therefore favourable to an optimum production of cellulolytic and/or hemicellulolytic enzymes.

According to the method of the present invention, addition of the carbon-containing inductive substrate is started as soon as the dissolved oxygen partial pressure in the medium is greater than value $Po_{2max}$ and stopped as soon as the dissolved oxygen pressure in the medium is below value $Po_{2min}$. Values $Po_{2min}$ and $Po_{2max}$ are determined according to the oxygen critical pressure and to the oxygen saturation pressure $Po_{2sat}$ of the medium when the bioreactor is started.

Value $Po_{2min}$ has to be greater than the critical pressure $Po_{2critical}$ below which the microorganism metabolism is affected and less than 95% of the saturation oxygen partial pressure $Po_{2sat}$ set when starting the bioreactor. $Po_{2min}$ preferably ranges between 10 and 60% of $Po_{2sat}$.

Value $Po_{2max}$ has to be at least 5% greater than value $Po_{2min}$. It can represent 100% of the oxygen partial pressure $Po_{2sat}$. $Po_{2max}$ preferably ranges between 30 and 70% of $Po_{2sat}$.

According to a more preferred embodiment, $Po_{2max}$ preferably ranges between 40 and 60% of $Po_{2sat}$ and $Po_{2min}$ preferably ranges between 30 and 50% of $Po_{2sat}$.

The carbon-containing inductive substrate is selected from among lactose, xylose, cellobiose, sophorose, residues obtained after ethanolic fermentation of the monomeric sugars of the enzymatic hydrolysates of cellulosic biomass and/or a crude extract of hydrosoluble pentoses from the pretreatment of a cellulosic biomass.

According to a preferred embodiment, the substrate is supplied in solution.

An aqueous solution comprising the carbon-containing inductive substrate selected for the enzyme production stage is prepared at a concentration of 10 to 800 g/L, preferably 150 to 600 g/L.

The aqueous solution comprising the carbon-containing inductive substrate is preferably a lactose solution.

Advantageously, a 250 g/L lactose solution is used.

The carbon-containing substrate used during the batch stage is selected from among glucose, galactose, glycerol, residues obtained after ethanolic fermentation of the monomeric sugars of the enzymatic hydrolysates of cellulosic biomass and/or a crude extract of hydrosoluble pentoses from the pretreatment of a cellulosic biomass.

The cellulolytic microorganism is selected from among fungi or other modified microorganisms (yeasts, bacteria). Preferably, the cellulolytic microorganism belongs to the *Trichoderma*, *Aspergillus*, *Penicillium* and *Schizophyllum* genera, and more preferably to the *Trichoderma reesei* species.

The method described in the present invention provides regulation of the supply of carbon-containing inductive substrate according to the dissolved oxygen partial pressure in the medium. A regulation according to the carbon dioxide production rate or to the dioxygen consumption rate calculated from the gas composition measured at the outlet would be an equivalent means of implementing the present invention.

EXAMPLES

Among the following examples, Example 1 presents the reference fermentation using lactose as the production carbon-containing substrate with an optimized supply rate of 35 to 45 $mg \cdot g^{-1} \cdot h^{-1}$ allowing a high protein production.

Example 2 presents the same experiment with a doubled carbon-containing substrate supply rate during the production stage. This example has led to a great biomass accumulation. It shows the risk involved when the carbon-containing substrate supply rate is higher than the optimum supply rate.

Examples 3 to 5 are in accordance with the method of the present invention. Example 3 uses the same supply rate as Example 1 and Example 4 the same supply rate as Example 2. The latter example shows the robustness of the method since it has led to a high protein production and no biomass accumulation has been observed during the production stage. Example 5 illustrates a larger oscillation range.

Example 1 (Comparative)

Enzyme Production According to a Conventional Fermentation Method as Described in Patent FR-B-2,811,753

The production of cellulases is achieved in a mechanically stirred fermenter. The mineral medium has the following composition: KOH 1.66 g/L, 85% $H_3PO_4$ 2 mL/L, $(NH_4)_2SO_4$ 2.8 g/L, $MgSO_4$, 7 $H_2O$ 0.6 g/L, $CaCL_2$ 0.6 g/L, $MnSO_4$ 3.2 mg/L, $ZnSO_4$, 7 $H_2O$ 2.8 mg/L, $CoCl_2$ 10 4.0 mg/L, $FeSO_4$, 7 $H_2O$ 10 mg/L, Corn Steep 1.2 g/L, anti-foaming agent 0.5 mL/L.

The fermenter containing the mineral medium is sterilized at 120° C. for 20 minutes, the glucose carbon-containing source is sterilized separately at 120° C. for 20 minutes, then sterilely added in the fermenter so as to have a final concentration of 15 g/L. The fermenter is seeded at 10% (v/v) with a liquid preculture of the CL847 *Trichoderma reesei* strain. The mineral medium of the preculture is identical to that of the fermenter, except for the addition of 5 g/L potassium phthalate as a pH buffering agent. The preculture fungus growth is achieved using glucose as the carbon-containing substrate, at a concentration of 30 g/L. The inoculum growth lasts for 2 to 3 days and is carried out at 28° C. in a stirred incubator. Transfer to the fermenter is performed if the residual glucose concentration is below 15 g/L.

The experiment carried out in the bioreactor comprises two stages:

a growth stage on glucose carbon-containing substrate (initial concentration 15 g/L) at a temperature of 27° C. and a pH value of 4.8 (regulated by 5.5 M ammonia). Aeration is 0.5 vvm (volume/volume/minute) and the dissolved oxygen partial pressure in the medium is 40% of $Po_{2sat}$;

an enzyme production stage. When the initial substrate of the fermenter is depleted, the 250 g/L lactose solution is injected continuously at 2 mL/h corresponding to a supply rate of 35 to 45 mg per g of cells and per hour up to 200 hours. The temperature is lowered to 25° C. and the pH value is maintained at 4 until the end of the culture. The pH value is regulated by adding a 5.5 N ammonia solution that provides the nitrogen required for synthesis of the proteins secreted. The dissolved oxygen content is maintained at 40% of $Po_{2sat}$.

Enzyme production is monitored by determining the extracellular protein concentration by means of the Lowry method and BSA standard, after mycelium separation by filtering or centrifuging. The cellulolytic activities determined are:

filter paper activity (FPU: filter paper unit) allowing to determine the overall activity of the endoglucanase and exoglucanase enzymatic pool;

aryl β-glucosidase activity.

The FPU activity is measured on Whatman No. 1 paper (a procedure recommended by the IUPAC Commission of Biotechnology) at an initial concentration of 50 g/L; the test sample of the enzymatic solution to be analyzed that releases the equivalent of 2 g/L glucose (colorimetric determination) in 60 minutes is determined. The principle of filter paper activity is to determine by the DNS (dinitrosalicylic acid) method the amount of reduced sugars released from a Whatman No. 1 paper.

The substrate used to determine the aryl β-glucosidase activity is p-nitrophenyl β-D-glucopyranoside (PNPG). It is cleaved by the β-glucosidase that releases the p-nitrophenol.

An aryl β-glucosidase activity unit is defined as the amount of enzyme required to produce 1 µmol p-nitrophenol from PNPG per minute and it is expressed in IU/mL.

The specific activities are obtained by dividing the activities expressed in IU/mL by the protein concentration. They are expressed in IU/mg.

The analytical determinations on the final must give the following results:
Biomass g/L 14.5
Proteins g/L 35.6
FPU IU/mL 18.7
Specific FPU IU/mg 0.52
Specific aryl β-glucosidase IU/mg 0.95.

Example 2 (Comparative)

Production of Enzymes with a Doubled Carbon-Containing Substrate Supply Rate During the Fed-Batch Stage in Relation to Example 1

Enzyme production is carried out under the same conditions as in Example 1. After 30 hours of growth, after depletion of the initial substrate, the fed-batch solution is injected at a supply rate that is doubled (4 mL/h instead of 2 mL/h) in relation to the experiment of Example 1. This leads to a significant biomass formation and to a low protein production. The production yield of proteins in relation to the carbon-containing substrate consumed is 0.1 g/g, whereas it is 0.3 g/g in Example 1.

The analytical determinations on the final must give the following results:
Biomass g/L 35.4
Proteins g/L 16.8
FPU IU/mL 11.7
Specific FPU IU/mg 0.70
Specific aryl β-glucosidase IU/mg 2.02.

Example 3 (According to the Invention)

Production of Enzymes by Regulating the Sugar Supply Through Regulation of the Dissolved Oxygen Partial Pressure in the Medium (Supply Rate 2 mL/h)

Enzyme production is carried out under the same conditions as in Example 1. After depletion of the carbon-containing substrate of the growth stage, the aeration flow rate is maintained at 0.5 vvm and stirring at 800 rpm, which allows, in the case of the fermenter used, to have a Kla value above 70 $h^{-1}$. The carbon-containing substrate is supplied according to the value of $Po_2$. Substrate supply is started when the oxygen partial pressure is greater than 50% of the saturation oxygen pressure with a supply rate of 2 mL/h and it is stopped when it is less than 40% of the saturation oxygen partial pressure (see FIG. 1).

The analytical determinations on the final must give the following results:
Biomass g/L 13.5
Proteins g/L 40.6
FPU IU/mL 28.1
Specific FPU IU/mg 0.69
Specific aryl β-glucosidase IU/mg 1.97.

The final production yield of proteins in relation to the carbon-containing substrate is 0.4 g/g. The specific activity FPase of the enzymatic cocktail produced is improved by 33%.

Example 4

Production of Enzymes by Regulating the Sugar Supply Through Regulation of the Oxygen Partial Pressure with a Doubled Supply Rate in Relation to Example 3 (Supply Rate 4 mL/h)

Enzyme production is carried out under the same conditions as in Example 3. The carbon-containing substrate is supplied according to the value of $Po_2$. Substrate supply is started when the oxygen partial pressure is greater than 50% of the saturation oxygen pressure with a supply rate of 4 mL/h instead of 2 mL/h and it is stopped when it is less than 40% of the saturation oxygen pressure. This allows to test the effect of a larger sugar supply.

This example shows the robustness of the method. Doubling the supply rate does not lead to a biomass accumulation as in the case of Example 2, thanks to regulation. This means that, even if the carbon-containing substrate concentration in the supply tray is variable (which may occur on an industrial scale), the method self regulates and maintains the optimum supply rate for enzyme production.

The analytical determinations on the final must give the following results:
Biomass g/L 16.1
Proteins g/L 43.6
FPU IU/mL 33.9
Specific FPU IU/mg 0.78
Specific aryl β-glucosidase IU/mg 1.60.

The final production yield of proteins in relation to the carbon-containing substrate is 0.4 g/g. The specific activity FPase of the enzymatic cocktail produced is improved by 50% in relation to Example 1.

Example 5

Production of Enzymes by Regulating the Sugar Supply by an Oscillation of the Oxygen Partial Pressure Between 20 and 80%

Enzyme production is carried out under the same conditions as in Example 4. The carbon-containing substrate is supplied according to the value of $Po_2$. Substrate supply is started when the oxygen partial pressure is greater than 80% of the saturation oxygen pressure with a supply rate of 4 mL/h and it is stopped when it is less than 20% of the saturation oxygen pressure. This allows to test the effect of a wider oscillation range.

The oscillations of $Po_2$ and the fed-batch solution supply rate are shown in FIG. 2.

The analytical determinations on the final must give the following results:
Biomass g/L 13.6
Proteins g/L 21.8
FPU IU/mL 20.4
Specific FPU IU/mg 0.93
Specific aryl β-glucosidase IU/mg 2.14.

The final production yield of proteins is lower because the amount of substrate injected is smaller. It can however be noted that the specific activities of the enzymatic cocktail are higher than those of Example 4 (oscillation of $Po_2$ between 40 and 50%). The conditions applied in Example 4 are more interesting because they allow to have a higher productivity and yield.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding FR application Ser. No. 10/01211, filed Mar. 26, 2010, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method of producing cellulolytic and/or hemicellulolytic enzymes by a cellulolytic microorganism in a stirred and aerated bioreactor, comprising a growth stage in the presence of a carbon source and a production stage in the presence of a carbon-containing inductive substrate, wherein the supply of carbon-containing inductive substrate during the production stage is regulated according to the dissolved oxygen partial pressure in the growth medium, said pressure oscillating between two values $Po_{2min}$ and $Po_{2max}$, the value of $Po_{2min}$ being greater than the critical pressure $PO_{2critical}$ below which the activity of the microorganism is affected and less than 95% of the saturation oxygen partial pressure $Po_{2sat}$ set when starting the bioreactor, and the value of $Po_{2max}$ being at least 5% greater than $Po_{2min}$, addition of the carbon-containing inductive substrate being started as soon as the dissolved oxygen partial pressure in the medium is greater than value $Po_{2max}$ and stopped as soon as the dissolved oxygen pressure in the medium is below value Po2min.

2. A method as claimed in claim 1, wherein $Po_{2max}$ ranges between 30 and 70% of $Po_{2sat}$ and $Po_{2min}$ ranges between 10 and 60% of Po2sat.

3. A method as claimed in claim 2, wherein $Po_{2max}$ ranges between 40 and 60% of $Po_{2sat}$ and $Po_{2min}$ ranges between 30 and 50% of Po2sat.

4. A method as claimed in claim 1, wherein the carbon-containing inductive substrate is selected from among lactose, xylose, cellobiose, sophorose, residues obtained after ethanolic fermentation of the monomeric sugars of the enzymatic hydrolysates of cellulosic biomass and/or a crude extract of hydrosoluble pentoses from the pretreatment of a cellulosic biomass.

5. A method as claimed in claim 1, wherein the substrate is supplied in solution.

6. A method as claimed in claim 5, wherein the carbon-containing inductive substrate selected for the enzyme production stage is at a concentration of 10 to 800 g/L.

7. A method as claimed in claim 5, wherein the carbon-containing inductive substrate is a lactose solution.

8. A method as claimed in claim 1, wherein stifling and aeration of the bioreactor are set at a predetermined value allowing said bioreactor to have an oxygenation capacity corresponding to a Kla value ranging between 50 and 150 h$^{-1}$.

9. A method as claimed in claim 1, wherein the cellulolytic microorganism is selected from among fungi belonging to the *Trichoderma, Aspergillus, Penicillium* and *Schizophyllum* genera.

10. A method as claimed in claim 9, wherein the cellulolytic microorganism belongs to the *Trichoderma reesei* species.

11. The method of claim 5, wherein the carbon-containing inductive substrate selected for the enzyme production stage is at a concentration of 150 to 600 g/L.

12. The method of claim 5, wherein the carbon-containing inductive substrate is a lactose solution at a concentration of 250 g/L.

13. The method of claim 1 wherein the method is performed in a batch process.

\* \* \* \* \*